United States Patent
Figueras et al.

(10) Patent No.: US 8,604,246 B2
(45) Date of Patent: Dec. 10, 2013

(54) SINGLE STEP CATALYTIC PREPARATION OF PARA-AMINOPHENOL

(75) Inventors: Francois Figueras, Lyons (FR); Abhay Deshpande, Lyons (FR)

(73) Assignees: Centre National de la Recherche Scientifique (C.N.R.S.), Paris (FR); Council of Scientific & Industrial Research, New Delhi (IN); Vinati Organics Ltd (V.O.L.), Maharashtra (IN)

( * ) Notice: Subject to any disclaimer, the term of this patent is extended or adjusted under 35 U.S.C. 154(b) by 424 days.

(21) Appl. No.: 12/741,655

(22) PCT Filed: Nov. 7, 2008

(86) PCT No.: PCT/EP2008/065100
§ 371 (c)(1), (2), (4) Date: Oct. 29, 2010

(87) PCT Pub. No.: WO2009/060050
PCT Pub. Date: May 14, 2009

(65) Prior Publication Data
US 2011/0092740 A1    Apr. 21, 2011

(30) Foreign Application Priority Data
Nov. 7, 2007 (EP) .................................. 07291339

(51) Int. Cl.
*C07C 213/02* (2006.01)
*C07C 209/36* (2006.01)

(52) U.S. Cl.
USPC ........................................................ 564/418

(58) Field of Classification Search
USPC ........................................................ 564/418
See application file for complete search history.

(56) References Cited

U.S. PATENT DOCUMENTS

| | | |
|---|---|---|
| 3,683,025 A * | 8/1972 | Pons .............................. 564/417 |
| 6,028,227 A | 2/2000 | Chaudhari et al. |
| 2005/0175525 A1 | 8/2005 | Fu et al. |

FOREIGN PATENT DOCUMENTS

| | | |
|---|---|---|
| CN | 1426964 A | 7/2003 |
| CN | 1559915 A | 1/2005 |
| GB | 610549 A | 10/1948 |
| GB | 1181969 A | 2/1970 |
| JP | 61056158 A | 3/1986 |

OTHER PUBLICATIONS

Komatsu T et al, "Gas phase synthesis of para-aminophenol from nitrobenzene on Pt/zeolite catalysts", Applied Catalysis A: General, Nov. 25, 2004, pp. 95-102, vol. 276, No. 1-2, Elsevier Science, Amsterdam, NL, XP004613245.

Song Xet al, "Sulfated Zirconia-Based Strong Solid-Acid Catalysts: Recent Progress" Catalysis Reviews: Science and Engineering, 1996, pp. 329-412, vol. 38, No. 2, Marcel Dekker Inc. New York, US, XP001536474.

Zyuzin et al, "X-ray, Raman and FTIRS studies of t he microstructural evolution of zirconia particles caused by the thermal treatment", Journal of Solid State Chemistry, Oct. 1, 2006, pp. 2965-2971, vol. 179, No. 10, Orlando, FL, US, XP005624309.

Cesario Franci Scodas Virgens et al, "Influence of the preparation method of the textural properties of zirconia" Reaction Kinetics and Catalysis Letters, Jan. 1, 2005, pp. 183-188, vol. 84, No. 1, Kluwer Academic Publishers, DO, XP019265328.

Liu, Qiyong et al, "Process for Production of Superfine Zirconia", 2005, XP002489261, Abstract.

Chen, Ling, et al, "Method for Preparing Zirconium Oxide Nanopowers by Ultrasonic Sol-Gel Process", 2005, XP002489262, Abstract.

International Search Report in Corresponding Application PCT/EP2008/065100 dated Jun. 4, 2009.

* cited by examiner

*Primary Examiner* — Brian J Davis
(74) *Attorney, Agent, or Firm* — Young & Thompson

(57) ABSTRACT

The method of using a bi-functional catalyst for the one-step preparation of para-aminophenol. The catalyst includes a mixture of a hydrogenation noble metal and a zirconium sulfate. Also, an improved single-step process for the preparation of para-aminophenol from nitrobenzene, in an aqueous medium, using the bi-functional catalyst.

20 Claims, No Drawings

SINGLE STEP CATALYTIC PREPARATION OF PARA-AMINOPHENOL

The present invention relates to the use of a bi-functional catalyst for the one-step preparation of para-aminophenol. The present invention also relates to an improved single step bi-functional catalysis process for the preparation of para-aminophenol. More particularly the process relates to the preparation of para-aminophenol from nitrobenzene, in an aqueous medium, using a bi-functional and eco-friendly catalyst.

para-Aminophenol ("p-aminophenol" or "PAP" in the following specification) is a well known and very useful industrial chemical. It is for example used as an intermediate in the production of pharmaceuticals such as paracetamol, in the production of dyestuffs such as sulphur dyes, and in making photographic chemicals.

The synthesis of paracetamol by acylation of p-aminophenol with acetic acid has been for example reported in U.S. Pat. No. 6,215,024. The most difficult step is the synthesis of PAP. This is industrially achieved in two steps: hydrogenation of nitrobenzene to phenylhydroxylamine, followed by the isomerisation into PAP.

Conventionally, PAP is prepared by hydrolysing para-nitrochlorobenzene to para-nitrophenol. Hydrogenation of para-nitrophenol to PAP is then carried out using a Fe/HCl catalyst. This multi-step process requires a quite large quantity of iron (catalyst precursor). Consequently, the production of iron-iron oxide sludge is large, creating serious effluent problems. The work-up of the reaction crude is cumbersome. The quantity of iron used is very important for the faster reduction rate.

An important commercial process for the preparation of para-aminophenol involves the catalytic hydrogenation of nitrobenzene ("NB") in acidic medium using supported platinum-based catalysts. In this process phenylhydroxylamine ("PHA") is first formed and this intermediate immediately rearranges, in the presence of acid, to PAP, according the well known Bamberger rearrangement. However, under these conditions, a significant amount of aniline as by-product is formed.

A first improvement was presented by Rylander et al. (DE 2118334), based on the inhibition of the concurrent reaction of aniline formation by the addition of dimethylsulphoxide (DMSO) to the reaction medium containing nitrobenzene and a Pt/C catalyst (5% Pt). The reaction performed in a solution of sulphuric acid ($H_2SO_4$) yields PAP.

A recent work by Ryong Ryoo et al. (*Stud. Surf. Sci. Cat.*, 135, (2001), 4710) reported that a 5% Pt on mesoporous carbon of high surface area was advantageous and permitted to reach 72% selectivity into PAP and 81% conversion of nitrobenzene, in a reaction performed in a solution of $H_2SO_4$. The kinetics of this reaction have been studied and modelled by Rode, Vaidya and Chaudhari (*Org. Proc. Res. Devel.*, 3(6), (1999), 465-470).

Caskey et al. (EP 85890 and EP 85511), replaced DMSO by diethylsulphide, with the same Pt/C catalyst, and performed the reaction in two steps: the first at 18-20° C., in the presence of DMS O and $NH_3$; the second consisted in the isomerisation of phenylhydroxylamine by $H_2SO_4$ at 70° C. The selectivity into PAP reached 90%.

Lee et al. (U.S. Pat. No. 4,885,389) reported the use of organic acids, with relatively low results. Medcalf (U.S. Pat. No. 4,051,187) reports the use of rhodium catalysts. Le Ludec (U.S. Pat. No. 3,927,191) reported the selective hydrogenation of nitro aromatics into hydroxylamines in the presence of basic additives such as pyridine. Sharma (U.S. Pat. No. 5,166, 435) used phosphines or phosphites to selectively hydrogenate nitroaromatics to hydroxylamines.

Dunn (U.S. Pat. No. 4,264,529) has reported the use of platinum on γ-alumina in conjunction with sulphuric acid for the hydrogenation of nitrobenzene to yield PAP. Derrenbacker (U.S. Pat. No. 4,307,249) added a surfactant to the reaction medium in order to increase the gas-liquid interface. Klausener (U.S. Pat. No. 5,545,754) used a reaction mixture containing sulphuric acid and a miscible organic solvent.

The first attempt to use pure heterogeneous catalysis for the conversion of nitrobenzene into p-aminophenol is due to Chaudhari et al. (U.S. Pat. No. 6,028,227), who used a platinum catalyst supported by a solid acid consisting of an acid resin. The preparation of p-aminophenol is achieved in one single step. However if the nitrobenzene conversion was high (97%), the selectivity of PAP was low (15%), and that of aniline 85%. The authors claimed many solid acids selected from the group consisting of ion exchange resins, heteropolyacids, synthetic and natural acidic clays, and acidic zeolites mainly silico-aluminates and zeolites. Using a nickel catalyst, the conversion was reduced to 14%, and the selectivity to 14%. The same authors also reported the selective hydrogenation of nitrophenol into PAP (*Org. Proc. Res. Dev.*, 7, (2003), 202).

Komatsu et al (*Applied Catalysis*, 2004, 276, 95-102) have reported a process in gaseous phase for the synthesis of p-aminophenol by using a solid catalyst consisting of metal particles supported on acidic zeolites. By using H-ZSM-5 zeolite the selectivity is of 66%. However, aniline and o-aminophenol are defined to be by-products of the reaction.

All attempts reported up to now to use heterogeneous catalysis are disappointing since the yields and selectivities are low. The catalysts used for hydrogenation of nitrobenzene to p-aminophenol reported in the literature are Pt, Pd, Ru, and $PtO_2$. Among these catalysts, however, Pt is the most active for this system but it is very costly. All these being noble metal the process becomes cost intensive. It also demands to use the same catalyst for several times and also to recover the metal from deactivated catalyst in order to make the process economical.

Moreover, in these processes, the inherent drawback is the use of excess sulphuric acid that requires neutralisation to produce enormous amounts of salt at the end of the reaction. The reaction medium is thus highly corrosive and it is necessary to use a special steel reactor.

A first objective of the present invention is to provide a bi-functional catalyst for use in a single step process of hydrogenation of nitrobenzene (NB) to phenylhydroxylamine and isomerisation to para-aminophenol (PAP) with a high NB conversion rate and a high selectivity to PAP.

Another objective of the invention relates to a single step process for the preparation of p-aminophenol using bi-functional heterogeneous catalysis, in which dilute sulphuric acid is replaced by a solid acid.

Song et al (*Catalysis Review: Science and Engineering*, 1996, 38(2), 329-412) reported the use of zirconium sulphate as a solid catalyst for the replacement of sulphuric acid solution. Nevertheless the authors do not report the use of such catalyst for the one step reaction of nitrobenzene to para-aminophenol.

Another objective is to increase the selectivity to para-aminophenol and to maintain a high conversion of nitrobenzene.

The present invention aims also at providing a catalyst with a low hydrogenation noble metal content, e.g. a low platinum content, and at using a non corrosive reaction medium, thereby avoiding the use of special steel for the reactor, and at using an environmental friendly and cheap solvent.

Still another objective is to use an acid catalyst which is easy to prepare and regenerate.

Further objectives will appear in the following description of the present invention. All the above-mentioned objectives are met in all or in part with the present invention.

As a first object, the present invention provides the use of a bi-functional catalyst for the one step reaction of nitrobenzene to para-aminophenol, wherein the bi-functional catalyst comprises a mixture of hydrogenation noble metal with zirconium sulfate.

The inventors have now discovered that the preparation of PAP from nitrobenzene (NB) provides good conversion of NB and good selectivity of PAP when using a specific solid acid catalyst, which comprises a supported hydrogenation noble metal and zirconium sulfate.

Indeed, zirconium sulfate has been found by the inventors to be catalytically active for the isomerisation of phenylhydroxylamine to PAP, while the hydrogenation noble metal is known to catalyse the hydrogenation reaction of NB to phenylhydroxylamine.

According to a feature of the invention, supported hydrogenation noble metal and zirconium sulfate are present as catalyst in the reaction medium in the form of a mixture. The expression "mixture" indicates a mechanical mixture and means that the hydrogenation noble metal and the zirconium sulfate are added separately, or as pre-mix to the reaction medium.

Carbon-supported zirconium sulfate has been described as an efficient water tolerant solid acid catalyst for esterification reactions (Catalysis Letters, vol 117, no 3-4, September 2007).

Zirconium sulfate has also been used to promote support materials consisting of $Al_2O_3$ on which noble metal from the platinum group are deposited in order to prepare high performance catalysts used in method for oxidizing a gas stream as described in US 2004/0028589.

Zirconium sulfate may be purchased or prepared according to a process which will be further described in the following specification. This process is also part of the present invention.

Zirconium sulfate for use in the present invention preferably is in crystallized form and presents a specific surface area of between 2 $m^2/g$ and 300 $m^2/g$, preferably between 2 $m^2/g$ and 100 $m^2/g$, more preferably between 2 $m^2/g$ and 50 $m^2/g$, for example about 3.5 $m^2/g$ to 10 $cm^2/g$.

The pore volume of the zirconium sulfate is generally greater than or equal to 0.6 $cm^3/g$, preferably greater than or equal to 0.2 $cm^3/g$, more preferably greater than or equal to 0.25 $cm^3/g$. Its average pore diameter is generally greater than or equal to 20 Ångströms, preferably greater than or equal to 30 Ångströms.

All above characteristics are measured using known methods in the art. As such, surface area is measured using a BET analysis of the isotherms of adsorption of nitrogen, pore volume corresponds to the volume adsorbed at P/P0=0.98 and pore diameter is determined by analysis of the isotherm using BJH theory as disclosed for example in "*The Determination of Pore Volume and Area Distributions in Porous Substances. I. Computations from Nitrogen Isotherms*", Elliott P. Barrett, Leslie G. Joyner, and Paul P. Halenda, *J. Am. Chem. Soc.,* 73(1), (1951), 373-380.

Advantageously, although not necessary, zirconium sulfate is activated by calcination prior use. Temperatures of calcination range from 400° C. to 700° C., preferably from 450° C. to 650° C., for example about 550° C. Calcination is conducted in air, most preferably with a temperature increase of 1-2° C./min.

Berk et al (GB 610,549) reported the preparation of basic zirconium sulphate by dissolving a zirconium source in a solution of sulphuric acid.

Zirconium sulfate may be obtained by dissolving zirconia (either commercially available or prepared as defined below) or zirconium salts for example chosen from among zirconyl chloride or oxycloride, zirconium acetate, zirconium alkoxides and the like, in a concentrated solution of sulphuric acid (e.g. 1N aqueous solution). Zirconia may for example be immersed into the acidic solution, stirred for a few minutes, preferably 5 to 30 minutes, for example 15 minutes until complete dissolution.

The ratio zirconia/sulphuric acid may vary, in general an excess of sulphuric acid is used. Satisfactory results were obtained by contacting 1 g zirconia with 15 mL 1N sulphuric acid.

The zirconium sulfate is then filtered off and washed several times with demineralised water, and dried in an oven (about 80-120° C.) overnight.

Finally, the zirconium sulfate is sieved to a specific diameter size, generally from 60 to 100 mesh, for example about 80 mesh and optionally calcined at the desired temperature, generally comprised between 450° C. and 750° C., preferably between 500-700° C., at a temperature rise of 1-2° C./min.

Fu et al (US 2005/0175525) reported a step of aging of the precipitate at a temperature higher than 60° C. in the process of preparation of zirconia ($ZrO_2$).

Zirconium sulfate may for example be prepared by dissolving zirconia in sulphuric acid, which zirconia may be prepared according to the following process comprising the steps of:

i) dissolving a zirconium dioxide (zirconia) precursor into water;
ii) allowing the precursor to hydrolyse to give zirconia as a precipitate, in a basic medium, generally at a constant pH greater than or equal to 9, advantageously 10;
iii) aging the precipitate, at a temperature ranging from 50° C. to 100° C., preferably from 70° C. to 90° C.;
iv) isolating and washing with water the aged precipitate; and
v) drying, powdering and sieving the obtained zirconia.

In the above preparation process, the zirconia precursor may be of any type known in the art, provided that it is transformed into zirconium hydroxide when contacted with water, in a basic medium. Such precursors may for example, be chosen from among zirconyl chloride or oxychloride, zirconium acetate, zirconium acetylacetonate, zirconium alkoxides, and the like.

Suitable bases that may be used to undergo the zirconia precursor hydrolysis are advantageously strong organic or inorganic, preferably inorganic, bases, so that the pH of the reaction medium is equal to or greater than 9, preferably 10. Examples of such bases are, but not limited to, ammonium hydroxide, sodium or potassium hydroxides, mixtures thereof and the like.

The hydrolysis product is then aged overnight at a temperature ranging from 50° C. to 100° C., preferably from 70° C. to 90° C., for example 80° C. The precipitate is then isolated, according to conventional methods (filtration, centrifugation, and the like) and washed several times with hot water.

In step v), the precipitate is dried, for example in an oven, at a temperature ranging from 50° C. to 100° C., preferably from 70° C. to 90° C., for example 80° C. for 1 to 3 days, e.g. 36-48 hours. Finally zirconia is powdered, generally ground in a mortar, and sieved to a diameter size, preferably ranging from 60 to 100 mesh, typically about 80 mesh, according to known methods.

The present invention therefore also relates to a process for the preparation of zirconium sulfate, comprising the steps of:
a) dissolving a zirconium dioxide (zirconia) precursor into water;
b) allowing the precursor to hydrolyse to give zirconia as a precipitate, in a basic medium, generally at a constant pH greater than or equal to 9, advantageously 10;
c) aging the precipitate, at a temperature ranging from 50° C. to 100° C., preferably from 70° C. to 90° C.;
d) isolating and washing with water the aged precipitate;
e) contacting the resulting hydrated zirconia with sulphuric acid;
f) dissolving the precipitate in the acidic medium;
g) removing water from the reaction medium, until a precipitate of zirconium sulfate is formed; and
h) drying the obtained zirconium sulfate.

In the above preparation process, the zirconia precursor may be of any type known in the art, as previously described. Suitable bases that may be used to undergo the zirconia precursor hydrolysis are also as depicted above.

In step e), the precipitate is contacted with an appropriate amount of sulphuric acid, generally about 1 mL of concentrated sulphuric for about 1 to 2 g of hydrated zirconia. The mixture is advantageously stirred until dissolution of the precipitate. A complete dissolution is compulsory, and when most of the precipitate is dissolved a turbid solution is obtained.

After complete, dissolution, water is removed from the solution, e.g. in a rotary evaporator, at a temperature of about 80° C., until a precipitate is obtained. The precipitated zirconium sulfate is collected and dried, at a temperature of about 120° C., during a couple of hours, say 5-24 hours, e.g. 10-18 hours.

Finally the zirconium sulfate may be activated by calcination in flowing air under conventional conditions known by the skilled in the art of solid catalysts, e.g. at a temperature of between 450° C. and 750° C., preferably 500° C. and 700° C., more preferably 550° C. and 650° C., advantageously at a temperature of about 625° C., for 2 to 8 hours, for example 4 hours.

The zirconium sulfate obtained from the above described process is particularly suitable for the single step preparation of PAP from NB, which will be further described in this specification.

As previously disclosed, zirconium sulfate is used in the process of the present invention as a catalyst together with a catalytically amount of a hydrogenation noble metal.

The expression "hydrogenation noble metal" means any noble metal known in the art for catalytic hydrogenation reaction, and preferably those conventionally used in the hydrogenation process of nitrobenzene (NB) to phenyl hydroxylamine (PHA).

"Hydrogenation noble metal" therefore includes platinum, palladium, ruthenium, platinum dioxide, nickel and the like, alone or in mixtures. Preferably the "hydrogenation noble metal" used in the process of the present invention, together with zirconium sulfate, is chosen from platinum and palladium or mixtures thereof, more preferably the "hydrogenation noble metal" is platinum.

The hydrogenation noble metal may be used as such, in any form known in the art, such as powder. Preferably the hydrogenation noble metal is used as a supported catalyst. In this case, the present inventors have established that the support may be of any type for the envisaged reaction of conversion of NB to PAP, i.e. the nature of the support has no, or hardly no effect, on the conversion rate and selectivity of said reaction.

Convenient supports for the hydrogenation noble metal may therefore be of any type and be chosen, for example and as a non limiting way, from among carbon, sulphated zirconia, zirconia, titanium dioxide, sulphated titanium dioxide, alumina, silica, mixed oxides of magnesium and lanthane, and the like, as well as mixtures of such supports.

For example, when the hydrogenation noble metal is platinum, the various types of supported platinum are referred to as Pt/C, Pt/ZrS, Pt/ZrO$_2$, Pt/TiO$_2$, Pt/Al$_2$O$_3$, Pt/SiO$_2$, or Pt/MgLaO and mixtures thereof.

Such supported platinum may be prepared according known techniques, such as for example those disclosed in J.-P. Brunelle, *Pure & Applied Chemistry*, 50, (1978), 124; or C. Marcilly et J.-P. Franck, *Revue Institut Français du Pétrole*, 39, (1984), 337. Additionally, specific preparations of supported platinum on various supports are presented in the examples that follow in the present specification.

The amount of hydrogenation noble metal in the support may vary in great proportions, depending on the characteristics of the hydrogenation metal itself, and on the nature of the support. Such usable amounts are known by the skilled in the art.

By way of illustration, and as a non limiting example, the content of platinum in the supported catalyst ranges between 0.01 and 10% by weight of the total weight of the supported catalyst, preferably between 0.1-5% by weight, for example 0.1%, 0.2-2% or 5% by weight.

The catalyst for use in preparing PAP from NB comprises, and preferably consists of, a mixture of zirconium sulfate with a supported hydrogenation noble metal. When the hydrogenation noble metal is platinum, the catalyst for use in preparing PAP from NB preferably is $Zr(SO_4)_2(H_2O)_4$+Pt/C, $Zr(SO_4)_2(H_2O)_4$+Pt/ZrS, $Zr(SO_4)_2(H_2O)_4$+Pt/ZrO$_2$, $Zr(SO_4)_2(H_2O)_4$+Pt/TiO$_2$, $Zr(SO_4)_2(H_2O)_4$+Pt/Al$_2$O$_3$, $Zr(SO_4)_2(H_2O)_4$+Pt/SiO$_2$, $Zr(SO_4)_2(H_2O)_4$+Pt/MgLaO, and mixtures thereof.

The weight ratio of zirconium sulfate to the hydrogenation noble metal may also vary in great proportions, for example from 100:1 to 1:100, preferably from 100:1 to 1:10, more preferably from 75:1 to 1:5, advantageously from 50:1 to 1:2, keeping in mind that the amount of hydrogenation catalyst (the hydrogenation noble metal) should be as low as possible as compared to the amount of the isomerisation catalyst (the zirconium sulfate).

Without any intention to be bound by theory, it is assumed that the hydrogenation reaction and the isomerisation reaction compete during the one-pot conversion of NB to PAP. While the first reaction runs rather quickly, the second one is slower. If a too high amount of hydrogenation catalyst is present, then the hydrogenation reaction tends to further hydrogenate the intermediate PHA to aniline, before the isomerisation reaction could take place to convert PHA to PAP.

The skilled artisan will therefore be able to determine with routine experiments, the appropriate ratio of hydrogenation noble metal to zirconium sulfate. For example, when the catalyst used is zirconium sulfate with 2% platinum supported on sulphated zirconia, the weight ratio zirconium sulfate to platinum on sulphated zirconia may range from 100:1 to 1:10, more preferably from 75:1 to 1:5, advantageously from 50:1 to 1:2. The following examples will present some convenient usable ratios of zirconium sulfate to supported platinum.

As an other example, when palladium is used in lieu of platinum, the amount of palladium is about five- to thirty-fold greater, since the activity of palladium is weaker as compared to that of platinum for the herein-described process.

The present inventors have evidenced that the use of a mixture of zirconium sulfate together with a hydrogenation noble metal, such as supported platinum- or palladium-based catalyst, was very efficient in terms of NB conversion and selectivity to PAP in the preparation process of para-aminophenol starting from nitrobenzene.

The present invention therefore provides, as a further object, a one-step process for an environmentally friendly synthesis of PAP, using heterogeneous acid catalysis. This process avoids the use of sulphuric acid and the formation of sulphates, and requires only very small amounts of hydrogenation noble metal. The catalyst comprises a mixture of zirconium sulfate together with a hydrogenation noble metal, such as platinum or palladium and the like, as defined above.

The solvent is water and the selectivity for PAP reaches 95% or more. The separation of products is simplified due to two factors: the selectivity is high and no sulphur or amine additives are required.

More particularly, the present invention provides a single step process for the preparation of para-aminophenol comprising the following steps:
A) contacting a mixture of nitrobenzene and water with a bi-functional catalyst comprising, and preferably consisting of, a mixture of a hydrogenation noble metal with zirconium sulfate;
B) placing the reaction mixture under hydrogen pressure;
C) allowing the reaction to take place;
D) terminating the reaction to obtain a reaction mixture containing para-aminophenol; and
E) isolating and recovering para-aminophenol from the reaction mixture.

The process of the present invention is detailed in the following description, but is not limited to such details in any way.

The hydrogenation noble metal used in the above process is as previously described in the present specification. Preferably, the hydrogenation noble metal is platinum or palladium, supported or not. According to a more preferred embodiment, the hydrogenation noble metal is supported platinum and may for example be chosen from $Zr(SO_4)_2(H_2O)_4+Pt/C$, $ZrS+Pt/ZrS$, $Zr(SO_4)_2(H_2O)_4+Pt/ZrO_2$, $Zr(SO_4)_2(H_2O)_4+Pt/TiO_2$, $Zr(SO_4)_2(H_2O)_4+Pt/Al_2O_3$, $Zr(SO_4)_2(H_2O)_4+Pt/SiO_2$, $Zr(SO_4)_2(H_2O)_4+Pt/MgLaO$, and mixtures thereof.

The process according to the invention comprises a first step A) wherein nitrobenzene (NB) is mixed with water in a volume ratio (water/NB) ranging from 50:1 to 1:50, preferably from 50:1 to 1:1, still more preferably from 40:1 to 3:1.

Advantageously the volume ratio (water/NB) ranges from 15:1 to 3:1.

The process does not exclude the use of dimethylsulphoxide (DMSO), as conventionally disclosed in the prior art (see for example Rylander et al. U.S. Pat. No. 3,715,397) in order to improve selectivity of PAP. However, the presence of DMSO in the reaction mixture of the present process is not compulsory: good conversion rates of NB as well as good selectivity of PAP have been obtained without the use of DMSO.

When DMSO is present in the reaction mixture, the volume ratio NB/DMSO generally ranges from 2:1 to 1:1. According to an embodiment, DMSO is added to the reaction mixture. According to another embodiment, no DMSO is used in the process of the present invention.

Preparations of PAP from NB are also generally conducted in alcohol solvents (see for example Rylander et al. U.S. Pat. No. 3,964,509). However, alcohols are not suitable for the process of the present invention, since they may have a deleterious action on the solid acid catalyst used therein.

Mention may also be made of the use of surfactants (for example as disclosed in U.S. Pat. No. 3,383,416) in the reaction mixture, for improving the surface of exchange between the solid catalyst (hydrogenation noble metal) and the liquid phase, and consequently accelerate the whole reaction process. Such use is however not preferred, although possible, since the complete removal of the surfactants from the obtained product (PAP) is a rather tedious operation.

The mixture of nitrobenzene, water, and optionally DMSO, is added with the mixture of hydrogenation noble metal with zirconium sulfate as previously described.

When platinum is the hydrogenation noble metal, the NB/platinum ratio (volume/Pt weight) is generally comprised between 1 and 600, preferably between 10 and 300, more preferably between 15 and 150, for example 15, 30, 45, 50 or 60, advantageously 60.

The ratio NB/zirconium sulfate (volume/weight) is generally comprised between 1 and 50, preferably between 2 and 30, more preferably between 3 and 15, for example 3, 6, 9 or 15.

The reaction medium is then placed under conventional hydrogenation conditions, such as for example in an autoclave under a hydrogen pressure ranging from 1 to 50 bars, preferably from 2 to 35 bars, more preferably from 3 to 20 bars, generally under hydrogen pressure of 10 bars. The reaction temperature may vary in the range 10° C. to about 200° C. depending on the kinetics of the reaction. Preferably the reaction temperature is set in the range of 50-100° C., for example 80° C.

Depending on the hydrogen pressure, the reaction temperature, and the amount of reagents and catalysts, the reaction may be run for a period of 10 minutes to 8 hours, generally for a period of 2 to 7 hours.

The progress of the reaction is monitored by taking and analysing samples from the reaction mixture. After completion of the reaction, the reaction mixture is removed from the autoclave, and the solid catalyst is separated from the liquid using conventional techniques, such as filtration for example. The filtrate is then extracted according to usual methods known by the skilled artisan, e.g. with organic solvents chosen from the group comprising toluene, cyclohexane, ethyl acetate or the like.

After extraction of the reaction mixture with an organic solvent and the separation of the aqueous layer, the latter is treated with an ammonia solution to adjust the pH of solution to 3-4, where PAP is precipitated partly. The solid thus obtains is separated by filtration. Again the filtrate is extracted with the organic solvent and aqueous layer is treated with ammonia solution to pH 7-8 to substantially precipitate PAP. The total solid thus obtained after the first and second extractions is washed with distilled water, dried and weighed.

Depending on the various embodiments of the process of the present invention, conversion of nitrobenzene ranges between 30-97%, and selectivity of para-aminophenol ranges between 60-99%.

The invention is further described with the help of the following examples which are given as illustrative purpose only and which do not intend to limit the scope of the invention in any way.

EXPERIMENTAL PART

Part A: Preparation of Catalysts

Example A1

Preparation of Zirconia 48 g of zirconyl chloride ($ZrOCl_2 \cdot XH_2O$, MW: 322.249) are dissolved in 375 mL water. The precipitation is carried out in a 3 L round bottomed flask, equipped with a mechanical stirrer and pH electrode for the online pH measurement.

Demineralised water (500 mL) is added to the flask initially so that the agitator and the tip of pH electrode dip in water. pH is adjusted at 10 by adding ammonium hydroxide solution.

Zirconium hydroxide is precipitated at constant pH=10 with the help of ammonium hydroxide. The zirconyl chloride solution is added to the precipitator at a rate of 15 mL/min and the pH is maintained at 10 with the help of addition of ammonium hydroxide solution (100 mL of concentrated ammonia (30%), diluted to 500 mL with demineralised water), throughout the addition. Both these solutions are added to the flask with the help of peristaltic pumps.

After completion, the precipitate is aged at 80° C. for 12 h after which, it is separated by centrifugation or filtration and washed 5 times with 800 mL of hot water (80° C.) to remove the excess ammonia and chloride ions. The precipitate is then transferred to a glass pan and dried in oven at 80° C. for 36-48 h. After drying, the solid is grinded and sieved to 80 mesh before storing.

Example A1

Preparation of Platinum on Sulphated Zirconia or Sulphated Titanium Dioxide: (General Method)

A stock solution is prepared by dissolving 1 g of chloroplatinic acid ($H_2PtCl_6 \cdot xH_2O$; M.W.: 409.82) in 100 mL demineralised water. Appropriate amount of this solution (corresponding to the desired platinum loading in the solid) is transferred to a round bottomed flask.

Ammonium hydroxide solution corresponding to 1.5-2 times the stoechiometric requirement is added to this flask and immersed in an oil bath maintained at 80° C.

The light brownish yellow colour of the solution disappears in 10-15 min. After the colour disappears, the temperature of the oil bath is increased so as to boil off excess ammonia.

After the ammonia is completely removed (test with wet pH paper), the solution is cooled to room temperature and desired amount of support (sulphated zirconia or sulphated titania) is added to the flask.

The slurry is stirred for 15 min and immersed in an oil bath maintained at 110° C. to boil off water. The residual solid is transferred to a glass pan with a minimum quantity of demineralised water and dried in oven at 80° C. overnight. The dry solid is sieved and filled in bottle.

Before use, the catalyst is calcined at 400° C. for 4 h in a current of air, with a temperature rise of 1-2° C./min.

After returning to room temperature, the air is replaced by nitrogen and purged for 10-15 min so as to displace the air completely. Nitrogen is then replaced by hydrogen and the catalyst is reduced at 250° C. for 2 h, with a temperature rise of 1-2° C./min.

After returning to room temperature, the hydrogen is again replaced with nitrogen and purged for 10-15 min. The catalyst is then transferred to an air tight bottle with minimum exposure to air.

The supported platinum catalyst can be also reduced directly without any calcination, and appears to be more active in that case.

Example A2

Preparation of 2% Platinum Supported on Sulphated Zirconia: (Specific Example)

1 g of $H_2PtCl_6 \cdot 6H_2O$ (M.W.: 409.82) is dissolved in 100 mL demineralised water. 10.6 mL of the above solution is taken in a 50 mL round bottom flask. 10 mL demineralised water and ~10 mL ammonia solution is added to it and the solution is stirred in an oil bath at 80° C. for 15-20 min.

At the end of this, the solution, which is originally yellow in colour, becomes colourless. Even after the disappearance of the yellow colour, presence of ammonia could be tested with the help of a wet pH indicator paper. The temperature of the oil bath is then increased to 114° C. so as to facilitate the removal of excess ammonia. Complete removal of ammonia is confirmed with the help of a wet pH indicator paper. The solution is finally allowed to cool to room temperature.

2 g sulphated zirconia, previously calcined at 650° C. for 4 h, are added to the cooled solution and the slurry is stirred for 10-15 min. The flask is then immersed in an oil bath maintained at 110° C. so as to evaporate water. Solid thus obtained is transferred to a glass petry dish with the help of minimal demineralised water. The solid is then dried in an oven at 80° C., overnight.

The dry catalyst thus obtained is calcined at 400° C. for 4 h in a current of air (100 mL/min). The temperature programme used for the furnace is, 0 h—25° C.; 7 h—400° C.; 11 h—400° C.; 11.5 h—25° C. The furnace temperature is allowed to reach 25° C. at the end without disturbing the assembly.

Air is then replaced by nitrogen for 10-15 min followed by hydrogen (50 mL/min), and the catalyst is reduced at 250° C. for 2 h. The temperature programme used for the furnace is, 0 h—25° C.; 4 h—250° C.; 6 h—250° C.; 11.5 h—25° C. The furnace temperature is allowed to reach 25° C. at the end without disturbing the assembly.

The hydrogen is finally replaced by nitrogen (100 mL/min) for 10-15 min. The reduced catalyst was then transferred to an airtight bottle with minimal exposure to atmosphere.

Here also the supported platinum catalyst can be reduced directly without calcination, following the same reduction procedure.

Example A3

Preparation of MgLaO

The following two solutions were prepared:
Solution A:

| | |
|---|---|
| Magnesium nitrate hexahydrate: | 99 g (0.386 mol) |
| Lanthanum nitrate hydrate: | 42 g (0.129 mol) |
| Demineralised water: | 500 ml |

Solution B:

| | |
|---|---|
| Potassium hydroxide: | 56 g (1.0 mol) |
| Potassium carbonate: | 36 g (0.26 mol) |
| Demineralised water: | 520 ml |

The precipitation is carried out in a 3 L round bottomed flask, equipped with a mechanical stirrer and pH electrode for the online pH measurement.

500 mL demineralised water is added to the flask initially so that the agitator and the tip of pH electrode dip in water. pH of this water is adjusted at 10 by adding requisite amount of solution B.

The precipitation was carried out at pH 10, with solution A being added at a rate of 25 mL/min and the rate of addition of solution B adjusted accordingly.

After the precipitation was complete, the slurry was aged at 80° C. for 12-15 h. The slurry was then filtered and the precipitate was washed with demineralised water 4-5 times. After water washes, the precipitate was washed with methanol two times.

The precipitate was finally transferred to a drying tray and dried overnight at 80° C. The dry solid was crushed to powder with a spatula and sieved to 80 mesh.

The powder thus obtained was calcined in a stream of air (100 mL/min) at 650° C. for 4 h, with temperature rise of 1-2° C./min.

Example A4

Preparation of Platinum on Zirconia, Titanium Dioxide or MgLaO (General Method)

A stock solution is prepared by dissolving 1 g of chloroplatinic acid ($H_2PtCl_6 \cdot xH_2O$; M.W.: 409.82) in 100 mL demineralised water. Appropriate amount of this solution (corresponding to the desired platinum loading in the solid) is transferred to a round bottomed flask.

Desired amount of support (zirconia, titanium dioxide (=titania) or MgLaO-3) is added to the flask. The slurry is stirred for 15 min and immersed in an oil bath maintained at 110° C. to boil off water. The residual solid is transferred to a glass pan with a minimum quantity of demineralised water and dried in oven at 80° C. overnight. The dry solid is sieved to 80 mesh and filled in bottle.

Before use, the catalyst is calcined at 400° C. for 4 h in a current of air, with a temperature rise of 1-2° C./min. After returning to room temperature, the air is replaced by nitrogen and purged for 10-15 min so as to displace the air completely. Nitrogen is then replaced by hydrogen and the catalyst is reduced at 250° C. for 2 h, with a temperature rise of 1-2° C./min.

After returning to room temperature, the hydrogen is again replaced with nitrogen and purged for 10-15 min. The catalyst is then transferred to an air tight bottle with minimum exposure to air.

Example A5

Preparation of Zirconium Sulfate: (According to the Invention)

48 g zirconyl chloride ($ZrOCl_2 \cdot XH_2O$, MW: 322.249) are dissolved in 375 mL water. Zirconium hydroxide is precipitated at constant pH=10 with the help of ammonium hydroxide.

The precipitate is aged at 80° C. for 12 h after which, it is separated by centrifugation and washed several times with hot water to remove the excess ammonia and chloride ions.

The wet precipitate is transferred to a conical flask. The centrifuge bottles are rinsed with 3-4 installments of water (total 200 mL). A solution of 21 mL concentrated sulphuric acid in 150 mL water is prepared and added to the conical flask. Slurry is stirred for 1 h at room temperature. Within this time, most of the precipitate dissolved and a turbid solution is obtained.

The turbid solution thus obtained is fed to a rotary evaporator and water is evaporated. The water bath is maintained at 80° C. during the evaporation. The solution becomes completely clear at higher temperature during the evaporation and remains so till the end. At the end, a white precipitate appears almost instantaneously. The evaporation is continued for 15-20 minutes after this.

The precipitate is then transferred to a glass pan with the help of minimum amount of ethanol and dried overnight at 120° C. After drying, the precipitate appears to be still a bit wet.

The zirconium sulfate thus obtained is calcined at a ramp of 1-2° C./min up to the desired temperature, maintained for 4 h.

Example B1

Using 2% Pt/$ZrO_2$ and Zirconium Sulfate of Example A5

75 mL water and 3 mL nitrobenzene (NB) are taken into a 100 mL capacity autoclave equipped with an efficient gas induction agitator, temperature sensor, sampling tube and a baffle.

0.01 g of 2% Pt/$ZrO_2$ (from MELCAT, ref F20922/1) and 0.5 g of zirconium sulfate obtained at Example A5 ($Zr(SO_4)_2(H_2O)_4$-A5), previously calcined at 650° C. for 4 h, are added and the reactor is closed.

Nitrogen is fed to the reactor (2.5 bar) and purged three times. Nitrogen is then replaced with hydrogen (10 bar) and purged three times. The agitation is started and maintained at 1200 rpm. Finally, the autoclave is heated to 8° C., with hydrogen pressure of 10 bar. Samples are then periodically withdrawn to monitor progress of reaction. The reaction is usually run for 7 hours.

The autoclave is allowed to cool to room temperature and then back to atmospheric pressure. The reaction mixture is removed, diluted in ethanol, and the composition of the products determined by HPLC using a UV detection.

Under the above conditions, preparation of PAP from NB was achieved with a NB conversion of 97% after 4 h of reaction, and a PAP selectivity of 76%.

Conversion and selectivity are determined from the chemical analyses of the reaction medium by the usual equations:

conversion=moles of nitrobenzene reacted/moles of initial nitrobenzene; and selectivity=moles of *PAP*(or *PHA* or *AN*)/moles of nitrobenzene reacted.

A similar experiment was conducted in a 700 mL capacity reactor with 56 mL nitrobenzene (NB) and 490 mL water (ratio water/NB=7.3). 0.14 g of 2% PT/$ZrO_2$ and 7 g of zirconium sulfate obtained at example A5 were added and the temperature was heated to 80° C. under hydrogen pressure of 20 bar.

Under the above conditions, preparation of PAP from NB was achieved with a NB conversion of 96.1% after 8 h of reaction and a PAP selectivity of 81.1%.

A similar experiment was conducted using DMSO (2 mL) together with water and NB. In that case, 99% conversion and 80% selectivity were obtained.

Other experiments were carried out, without DMSO, using a mixture Pt/ZrS reduced at 250° C.+$Zr(SO_4)_2(H_2O)_4$, leading to similar results.

Similar selectivity could be reached using either Pt/$ZrO_2$ (not sulphated), Pt/$TiO_2$ or Pt/MgLaO mixed with zirconium sulfate $Zr(SO_4)_2(H_2O)_4$-A5. With the mixture 2% Pt/$ZrO_2$ (0.01 g)+$Zr(SO_4)_2(H_2O)_4$ (0.5 g) at 80° C. and 10 bars hydrogen ($H_2$) the conversion reaches 81% and the selectivity to PAP 71%. Similar results have been obtained with Pt/$TiO_2$ and Pt/MgLaO showing that the support of platinum has no critical effect.

This is confirmed by the results obtained with a commercial Pt/C containing 1% Pt, as illustrated by the following experiments performed in the standard conditions (3 mL nitrobenzene, 75 mL water, temp 80° C.). Using as catalyst a mixture of 0.01 g 1% Pt/C+1.0 g $Zr(SO_4)_2(H_2O)_4$-A5 and 10 bars of hydrogen pressure, the conversion reaches 93% after 6 hours, with a selectivity to PAP of 92%. With a mixture of 0.01 g 1% Pt/C+0.5 g $Zr(SO_4)_2(H_2O)_4$-A5 and 20% bars of hydrogen pressure, the conversion reaches 62% after 6 hours, with a selectivity to PAP of 98%.

Examples B2-B8

Influence of the Amount of Catalyst

The platinum loading on the support has been changed to 0.1%, 0.5%, 1% and 2% using cationic exchange from Pt-amine, and the activity measured at 80° C., 3.8 bars hydrogen, with different amounts of Pt/$Zr(SO_4)_2(H_2O)_4$ catalyst of Example A5 ($Zr(SO_4)_2(H_2O)_4$-A5; 0.01, 0.1 and 0.3 g) with an amount of $Zr(SO_4)_2(H_2O)_4$-A5 of 0.1 g or 0.05 g. The catalytic results after 1 hour of reaction are reported in Table 1 below:

TABLE 1

| Example. # | Pt catalyst (g) | % Pt | $Zr(SO_4)_2(H_2O)_4$-A5 (g) | NB Conversion | AN Select[1] | PAP Select.[2] |
|---|---|---|---|---|---|---|
| B2 | 0.01 | 2.0 | 0.5 | 20.9 | 14.8 | 85.2 |
| B3 | 0.01 | 1 | 0.1 | 10.3 | 3.3 | 96.7 |
| B4 | 0.01 | 0.5 | 0.1 | 9.0 | 3.5 | 96.5 |
| B5 | 0.03 | 0.5 | 0.1 | 28.0 | 2.5 | 97.5 |
| B6 | 0.1 | 0.1 | 0.1 | 25.1 | 2.2 | 92.8 |
| B7 | 0.1 | 0.1 (chlor)[3] | 0.05 | 8.6 | 2.5 | 97.5 |
| B8 | 0.1 | 0.1 | 0.05 | 20.7 | 14.9 | 85.1 |

[1]Selectivity to aniline (calculated as indicated above).
[2]Selectivity to PAP (calculated as indicated above).
[3](chlor) = catalyst prepared from hexachloroplatinic acid.

As a conclusion:
Decreasing the amount of platinum from 1% to 0.5% has no effect either on rate or selectivity;
Increasing the amount of Platinum catalyst from 0.01 g to 0.03 g increases the conversion by 3, as expected, with a constant selectivity;
A decrease of the platinum loading to 0.1% induces an increase of activity. It is assumed this increase is linked to a better dispersion of platinum at low loading. This proposal is consistent with the observation of a low activity of the catalyst prepared by wet impregnation from the chloride salt.
The comparison of Examples B6 and B8 shows that an amount of zirconium sulfate of less than 0.1 g leads to a slight loss of conversion and selectivity. With the lower amount of acid catalyst, PHA appears in the products, probably because of the fact that isomerisation is not fast enough to convert all the intermediate.

Examples B9-B15

Influence of Zirconium Sulfate

Examples B9 to B15 have been conducted according to the process described in Example B1, using a constant amount of 0.1 g of 2% Pt/MgLaO, in association with various solid acid catalysts (0.5 g): zirconia, sulphated titania (titanium dioxide), a HBEA zeolite, a commercially available sulphated zirconia, and two zirconium sulfates prepared as in Example A5 ($Zr(SO_4)_2(H_2O)_4$-A5) with two different temperatures of calcination.

The results obtained after 1 hour reaction with 3 mL NB in 75 mL water, 80° C. and under 10 bars hydrogen pressure, are listed in the below Table 2.

TABLE 2

| Example # | Solid acid | NB conversion | Selectivity PHA | PAP | AN |
|---|---|---|---|---|---|
| B9 | $ZrO_2$ 922-1[4] | 93.9 | 14.5 | 38 | 47.4 |
| B10 | $Zr(SO_4)_2(H_2O)_4$-A5 calc. 650° C. | 94.3 | 10 | 51.3 | 38.7 |
| B11 | $Zr(SO_4)_2(H_2O)_4$-A5 calc. 625° C. | 97.2 | 0 | 76.1 | 23.9 |
| B12 | $Zr(SO_4)_2(H_2O)_4$-A5 calc. 550° C. | 79.2 | 0 | 95.3 | 4.7 |
| B13 | Sulphated $TiO_2$[5] | 96.5 | 0.5 | 9.1 | 90.3 |
| B14 | Sulphated $ZrO_2$ 922-1 | 91.7 | 22.8 | 17.3 | 59.6 |
| B15 | HBEA zeolite[6] | 74.8 | 7 | 6.5 | 86.4 |

[4]supplied by MEL Chemicals (Magnesium Electron, Inc.)
[5]prepared by sulphation of a titania gel supplied by Millenium Inorganic Chemicals.
[6]supplied by Zeolysts International (Si/Al = 25)

These results show that sulphated titania or HBEA zeolite is most probably not enough acid to complete the Bamberger rearrangement. Non-sulphated zirconia is inactive for this rearrangement (Example B9), and the best PAP selectivity is obtained with a zirconium sulfate prepared according to the process of the invention and calcined at a temperature of 550-625° C.

Isomerisation of Phenylhydroxylamine on Different Acid Catalysts

The importance of the acidity of the solid acid is confirmed by the separate study of the isomerisation of PHA to PAP, reported in Table 3 below summarising the results obtained for the conversion of PHA (prepared separately according to traditional procedures) at 80° C.: 109 mg of PHA added to 7 mL of water were reacted in the presence of 0.1 g of solid acid. The products are PAP, o-aminophenol, aniline and nitrobenzene.

The results show that HBEA zeolite, K10 or bentonite are very active but not selective for this reaction and form aniline and other products. Moreover different zirconium sulfates show the same high selectivity, but different conversion rates.

TABLE 3

| Sample | Reaction Time (min) | PHA Conversion | PAP selectivity |
|---|---|---|---|
| K10 (acid treated montmorillonite from Süd Chemie) | 30 | 100.0 | 17.6 |
| BEA zeolite | 30 | 49.1 | 61.6 |
| Bentonite-HPF | 30 | 99.6 | 25.8 |
| $SiO_2$—$SO_3H$[7] | 30 | 78.0 | 94.2 |
| Sulphated TiO2, calc 50° C. | 30 | 100 | 29.8 |
| ZrS (from LOBA zirconia) | 60 | 33.6 | 94.8 |
| $Zr(SO_4)_2(H_2O)_4$-exZrOCl$_2$ (calc 620° C.) | 30 | 35.1 | 99.9 |
|  | 60 | 47.3 | 96.8 |
| $Zr(SO_4)_2(H_2O)_4$ (calc 650° C.) | 30 | 23.2 | 97.0 |
|  | 60 | 40.0 | 92.1 |
| $Zr(SO_4)_2(H_2O)_4$-A5 calc 620° C. | 30 | 100 | 99.6 |
| ZrS Melcat 999-1 (calc 650° C.) | 30 | 21.8 | 94.5 |
|  | 60 | 39.1 | 95.2 |

[7]for example conventionally obtained from (MeO)$_3$Si-phenyl-SH oxidized with hydrogen peroxide.

Examples B16 and B17

Influence of the Amount of Platinum-Based Catalyst

Under the same conditions as in examples B9-B15, examples B16 and B17 of preparation of PAP from NB have been conducted. In these examples (1 hour reaction with 3 mL NB in 75 mL water, 80° C. and under 10 bars hydrogen pressure), the catalyst is a mixture of 2% Pt/MgLaO (0.05 g and 0.01 g respectively) and 0.5 g of $Zr(SO_4)_2(H_2O)_4$-A5 (calcination: 5500).

The results are listed in the following Table 4.

TABLE 4

| Example # | Amount Pt/MgLaO | NB conv. | PHA | PAP | AN | Uks | PAP sel. |
|---|---|---|---|---|---|---|---|
| B16 | 0.05 g | 98.9 | 0.0 | 7.8 | 90.5 | 0.6 | 7.9 |
| B17 | 0.01 g | 40.2 | 0.0 | 34.9 | 4.7 | 0.5 | 86.8 |

These results illustrate the fact that a high hydrogenation rate leads to a fast conversion, but to aniline and not to PAP; using the bi-functional catalyst supported platinum/zirconium sulfate, care should be given to the balance of the two functions of hydrogenation of NB to phenylhydroxylamine (PHA) and isomerisation of PHA to PAP.

Example B18

Using 1% Pt/ZrO$_2$ and Zirconium Sulfate of Example A5

Conversion of NB to PAP was conducted with the following conditions:

| | |
|---|---|
| NB amount: | 3 mL; |
| Water amount: | 75 mL; |
| Hydrogenation catalyst: | 0.02 g of 1% Pt/ZrO$_2$ heated to 250° C. (not calcined); |
| Zirconium sulfate: | 1 g $Zr(SO_4)_2(H_2O)_4$-A5 calcined at 625° C.; |
| Reaction time: | 4 hours; |
| Hydrogen pressure: | 10 bars; and |
| Reaction temperature: | 80° C. |
| | The results are: |
| NB conversion: | 90.2; and |
| PAP selectivity: | 85.2. |

Example B19

Using 1% Pt/MgLaO and $Zr(SO_4)_2(H_2O)_4$-A5

Conversion of NB to PAP was conducted with the following conditions:

| | |
|---|---|
| NB amount: | 3 mL; |
| Water amount: | 75 mL; |
| Hydrogenation catalyst: | 0.02 g of 1% Pt/MgLaO heated to 250° C. (not calcined); |
| Zirconium sulfate: | 1 g $Zr(SO_4)_2(H_2O)_4$-A5 calcined at 625° C.; |
| Reaction time: | 4 hours; |
| Hydrogen pressure: | 10 bars; and |
| Reaction temperature: | 80° C. |
| | The results are: |
| NB conversion: | 80.2; and |
| PAP selectivity: | 97.8. |

Example B20

Using 2% Pt/MgLaO and $Zr(SO_4)_2(H_2O)_4$-A5

Conversion of NB to PAP was conducted with the following conditions:

| | |
|---|---|
| NB amount: | 3 mL; |
| Water amount: | 75 mL; |
| Hydrogenation catalyst: | 0.01 g of 2% Pt/MgLaO; |
| Zirconium sulfate: | 0.5 g $Zr(SO_4)_2(H_2O)_4$-A5 calcined at 625° C.; |
| Reaction time: | 4 hours; |
| Hydrogen pressure: | 10 bars; and |
| Reaction temperature: | 80° C. |
| | The results are: |
| NB conversion: | 97.2; |
| PAP selectivity: | 76.1; |
| PHA selectivity: | 0; and |
| Aniline selectivity: | 23.9. |

It should be noted that under the above conditions, no phenylhydroxylamine was obtained, thereby facilitating the separation PAP/aniline.

Example B21

Using 2% Pt/MgLaO and $Zr(SO_4)_2(H_2O)_4$-A5

Conversion of NB to PAP was conducted with the following conditions:

| | |
|---|---|
| NB amount: | 25 mL; |
| Water amount: | 50 mL; |
| Hydrogenation catalyst: | 0.1 g of 1% Pt/MgLaO; |
| Zirconium sulfate: | 1 g $Zr(SO_4)_2(H_2O)_4$-A5 calcined at 625° C.; |
| Reaction time: | 2 hours; |
| Hydrogen pressure: | 10 bars; and |
| Reaction temperature: | 80° C. |
| | The results are: |
| NB conversion: | 29.8; and |
| PAP selectivity: | 87.7. |

In this experiment, concentration of NB is higher than in the previous examples. No PHA was found in the reaction medium and a good selectivity to PAP was obtained after 2 hours of reaction.

The above results also evidence a remarkable advantage of the use and process of the invention: a small quantity of platinum is sufficient to yield PAP with a good selectivity. Increasing the amount of platinum in the mixture of catalysts is detrimental to PAP selectivity.

The process of the invention therefore involves a cheap and eco-friendly catalyst and is perfectly suited for industrial applications, especially as an intermediate process to paracetamol and other chemical, dyestuffs, and the like.

The invention claimed is:

1. A method of forming para-aminophenol in a one step reaction, comprising:
performing hydrogenation of nitrobenzene to para-aminophenol in the presence of a bi-functional catalyst, wherein the bi-functional catalyst comprises a mixture of a hydrogenation noble metal and zirconium sulfate.

2. The method according to claim 1, wherein the hydrogenation noble metal is selected from the group consisting of platinum, palladium, ruthenium, nickel and mixtures thereof.

3. The method according to claim 1, wherein the hydrogenation noble metal is platinum.

4. The method according to claim 1, wherein the hydrogenation noble metal is supported on a support selected from the group consisting of carbon, sulphated zirconia, zirconia, titanium dioxide, sulphated titanium dioxide, alumina, silica, mixed oxides of magnesium and lanthane, and mixtures thereof.

5. The method according to claim 1, wherein the zirconium sulfate is $Zr(SO_4)_2(H_2O)_4$.

6. The method according to claim 1, wherein the zirconium sulfate presents a specific surface area of between 2 $m^2/g$ and 300 $m^2/g$.

7. The method according to claim 1, wherein the bi-functional catalyst comprises a mixture selected from the group consisting of $Zr(SO_4)_2(H_2O)_4$+Pt/C, $Zr(SO_4)_2(H_2O)_4$+Pt/ZrS, $Zr(SO_4)_2(H_2O)_4$+Pt/ZrO_2, $Zr(SO_4)_2(H_2O)_4$+Pt/TiO_2, $Zr(SO_4)_2(H_2O)_4$+Pt/Al_2O_3, $Zr(SO_4)_2(H_2O)_4$+Pt/SiO_2, $Zr(SO_4)_2(H_2O)_4$+Pt/MgLaO, and mixtures thereof.

8. The method according to claim 1, wherein the weight ratio of zirconium sulfate to the hydrogenation noble metal ranges from 100:1 to 1:100.

9. A process for the preparation of para-aminophenol comprising the following steps:
A) contacting a mixture of nitrobenzene and water with a bi-functional catalyst comprising a mixture of a hydrogenation noble metal and zirconium sulfate;
B) placing the reaction mixture under hydrogen pressure;
C) allowing a reaction to take place;
D) terminating the reaction to obtain a reaction mixture containing para-aminophenol; and
E) isolating and recovering the para-aminophenol from the reaction mixture.

10. The process according to claim 9, wherein the hydrogenation noble metal is selected from the group consisting of platinum, palladium, ruthenium, nickel and in mixtures thereof.

11. The process according to claim 9, wherein the hydrogenation noble metal is supported platinum selected from the group consisting of Pt/C, Pt/ZrS, Pt/ZrO_2, Pt/TiO_2, Pt/Al_2O_3, Pt/SiO_2, Pt/MgLaO, and mixtures thereof.

12. The process according to claim 9, wherein the volume ratio of water/nitrobenzene is between 50:1 to 1:50.

13. The process according to claim 9, wherein the reaction mixture further comprises DMSO.

14. The process according to claim 9, wherein the zirconium sulfate is $Zr(SO_4)_2(H_2O)_4$.

15. The process according to claim 9, wherein the zirconium sulfate presents a specific surface area of between 2 $m^2/g$ and 300 $m^2/g$.

16. The process according to claim 9, wherein the bi-functional catalyst comprises a mixture selected from the group consisting of $Zr(SO_4)_2(H_2O)_4$+Pt/C, $Zr(SO_4)_2(H_2O)_4$+Pt/ZrS, $Zr(SO_4)_2(H_2O)_4$+Pt/ZrO_2, $Zr(SO_4)_2(H_2O)_4$+Pt/TiO_2, $Zr(SO_4)_2(H_2O)_4$+Pt/Al_2O_3, $Zr(SO_4)_2(H_2O)_4$+Pt/SiO_2, $Zr(SO_4)_2(H_2O)_4$+Pt/MgLaO, and mixtures thereof.

17. The process according to claim 9, wherein the weight ratio of zirconium sulfate to the hydrogenation noble metal ranges from 100:1 to 1:100.

18. The process according to claim 9, wherein the volume/weight ratio of nitrobenzene/zirconium sulfate is between 1 and 50.

19. The process according to claim 9, wherein the hydrogen pressure is between 1 and 50 bars.

20. The process according to claim 9, wherein the temperature of the reaction is in the range of 10° C. to about 200° C.

* * * * *

UNITED STATES PATENT AND TRADEMARK OFFICE
CERTIFICATE OF CORRECTION

PATENT NO.       : 8,604,246 B2                                    Page 1 of 1
APPLICATION NO. : 12/741655
DATED            : December 10, 2013
INVENTOR(S)      : Figueras et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 600 days.

Signed and Sealed this
Twenty-second Day of September, 2015

Michelle K. Lee
*Director of the United States Patent and Trademark Office*